(12) United States Patent
Hill et al.

(10) Patent No.: US 9,724,014 B2
(45) Date of Patent: Aug. 8, 2017

(54) ACTIVE DETECTION OF SENSOR TRANSITION FROM COVERED TO EXPOSED

(71) Applicant: St. Jude Medical, Atrial Fibrillation Division, Inc., St. Paul, MN (US)

(72) Inventors: Anthony D. Hill, Minneapolis, MN (US); D. Curtis Deno, Andover, MN (US); Ram Balachandran, Maple Grove, MN (US); Braden Eliason, Shoreview, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 379 days.

(21) Appl. No.: 13/797,014

(22) Filed: Mar. 12, 2013

(65) Prior Publication Data

US 2014/0275913 A1  Sep. 18, 2014

(51) Int. Cl.

| | | |
|---|---|---|
| *A61B 5/04* | (2006.01) | |
| *A61B 5/06* | (2006.01) | |
| *A61M 25/01* | (2006.01) | |
| *A61B 18/14* | (2006.01) | |
| *A61M 25/00* | (2006.01) | |
| *A61M 25/06* | (2006.01) | |

(Continued)

(52) U.S. Cl.
CPC ............ *A61B 5/065* (2013.01); *A61B 5/062* (2013.01); *A61B 5/063* (2013.01); *A61B 5/066* (2013.01); *A61B 34/20* (2016.02); *A61B 18/1492* (2013.01); *A61B 2034/2053* (2016.02); *A61B 2090/0811* (2016.02); *A61M 25/0097* (2013.01); *A61M 25/0662* (2013.01); *A61M 2025/0166* (2013.01); *A61M 2025/0675* (2013.01)

(58) Field of Classification Search
CPC ........ A61B 2018/1472; A61B 18/1492; A61B 2018/00577; A61B 2018/00875; A61B 2018/00702; A61B 2018/00827; A61N 1/40
USPC ................ 600/372–374, 381, 433–435, 481, 600/508–509
See application file for complete search history.

(56) References Cited

U.S. PATENT DOCUMENTS

| | | |
|---|---|---|
| 6,035,226 A | 3/2000 | Panescu et al. |
| 6,233,476 B1 | 5/2001 | Strommer |

(Continued)

FOREIGN PATENT DOCUMENTS

| | | |
|---|---|---|
| WO | 97/45157 | 12/1997 |
| WO | 2008/073214 | 6/2008 |

(Continued)

OTHER PUBLICATIONS

International Search Report for related PCT Application No. PCT/US2014/018700 dated Jun. 2, 2014, 5 pgs.

*Primary Examiner* — Joseph Stoklosa
*Assistant Examiner* — Brian M Antiskay
(74) *Attorney, Agent, or Firm* — Dykema Gossett PLLC

(57) ABSTRACT

An introducer may comprise a shaft and a proximal electrode. The shaft may have a proximal end portion and an interior lumen, the interior lumen configured to receive a catheter therethrough. The proximal electrode may be coupled with the proximal end portion and may be configured to act as an electrical source or sink so as to create an electrical field within the interior lumen. A position of an electrode coupled with the catheter may be determined according to the electrical field.

19 Claims, 5 Drawing Sheets

(51) Int. Cl.
 *A61B 34/20* (2016.01)
 *A61B 90/00* (2016.01)

(56) References Cited

U.S. PATENT DOCUMENTS

| | | |
|---|---|---|
| 6,498,944 B1 | 12/2002 | Ben-Haim et al. |
| 6,690,963 B2 | 2/2004 | Ben-Haim et al. |
| 6,788,967 B2 | 9/2004 | Ben-Haim et al. |
| 7,197,354 B2 | 3/2007 | Sobe |
| 7,263,397 B2 | 8/2007 | Hauck et al. |
| 7,386,339 B2 | 6/2008 | Strommer |
| 7,536,218 B2 | 5/2009 | Govari et al. |
| 8,343,096 B2 | 1/2013 | Kirschenman et al. |
| 2007/0060833 A1 | 3/2007 | Hauck |
| 2007/0066889 A1 | 3/2007 | Boese et al. |
| 2007/0078457 A1* | 4/2007 | Paul ............... A61B 18/1492 606/50 |
| 2008/0255470 A1 | 10/2008 | Hauck et al. |
| 2009/0262979 A1 | 10/2009 | Markowitz et al. |
| 2009/0264739 A1 | 10/2009 | Markowitz et al. |
| 2010/0174169 A1 | 7/2010 | Razavi |
| 2012/0010490 A1 | 1/2012 | Kauphusman et al. |
| 2012/0101355 A1* | 4/2012 | Gopinathan ....... A61B 5/02007 600/373 |
| 2013/0303886 A1 | 11/2013 | Ludwin et al. |

FOREIGN PATENT DOCUMENTS

| | | |
|---|---|---|
| WO | 2008-082802 | 7/2008 |
| WO | 2013/101270 | 7/2013 |
| WO | 2013/152335 | 10/2013 |

\* cited by examiner

ACTIVE DETECTION OF SENSOR TRANSITION FROM COVERED TO EXPOSED

BACKGROUND a. Technical Field

The instant disclosure relates to elongate medical devices, including detection of the positions of one or more sensors on an interior coaxial medical device relative to a shaft of an exterior coaxial medical device.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart. The catheter typically carries one or more electrodes, which may be used for ablation, diagnosis, or the like.

To insert the catheter into a patient's body or a target organ or site within the body, an introducer or sheath may be used. The introducer may be guided through the patient's vasculature through a portion of the path to a target site, for example, and the catheter may be inserted through the proximal end of the introducer, extended through the introducer, and extended out of the distal end of the introducer for guidance over the remainder of the path to the target site. Once at the target site, electrodes on the catheter may be used to collect electrophysiology (EP) data, to determine the position and orientation of the catheter, and for other purposes.

The foregoing discussion is intended only to illustrate the present field and should not be taken as a disavowal of claim scope.

BRIEF SUMMARY

An embodiment of an exterior coaxial elongate medical device may be configured to be coupled with an interior coaxial medical device having an interior electrode. The exterior coaxial elongate medical device may comprise a shaft, a handle, and a proximal electrode. The shaft may have a proximal end portion and an interior lumen, the interior lumen configured to receive the interior coaxial medical device therethrough. The handle may be coupled with the proximal end portion. The proximal electrode may be coupled with one of the proximal end portion and the handle and may be configured to act as an electrical source or sink so as to create an electrical field within the interior lumen. A position of the interior electrode may be determined according to the electrical field.

An embodiment of a method of determining the relative positions of an interior electrode coupled with an interior coaxial medical device and a shaft of an exterior coaxial medical device may comprise driving an electrical current between a proximal electrode coupled with a proximal end of the interior coaxial medical device and a distal electrode so as to create an electrical field within an interior lumen of the exterior coaxial medical device, at least a portion of the interior coaxial medical device disposed within the interior lumen. The method may further comprise measuring an electrical potential with the interior electrode according to the electrical field, and determining whether the interior electrode is within the shaft of the exterior coaxial medical device according to the measured electrical potential.

An embodiment of an electronic control unit (ECU) for determining the position of an interior electrode coupled with an interior coaxial medical device relative to a distal end opening of a shaft of an exterior coaxial medical device, the exterior coaxial medical device including an interior lumen configured to receive the interior coaxial medical device and a proximal electrode may be configured to drive an electrical current between the proximal electrode and a distal electrode so as to create an electrical field within the interior lumen of the exterior elongate medical device. The ECU may be further configured to measure an electrical potential with the interior electrode, and determine a position of the interior electrode relative to the distal opening of the exterior elongate medical device shaft according to the measured electrical potential.

DETAILED DESCRIPTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
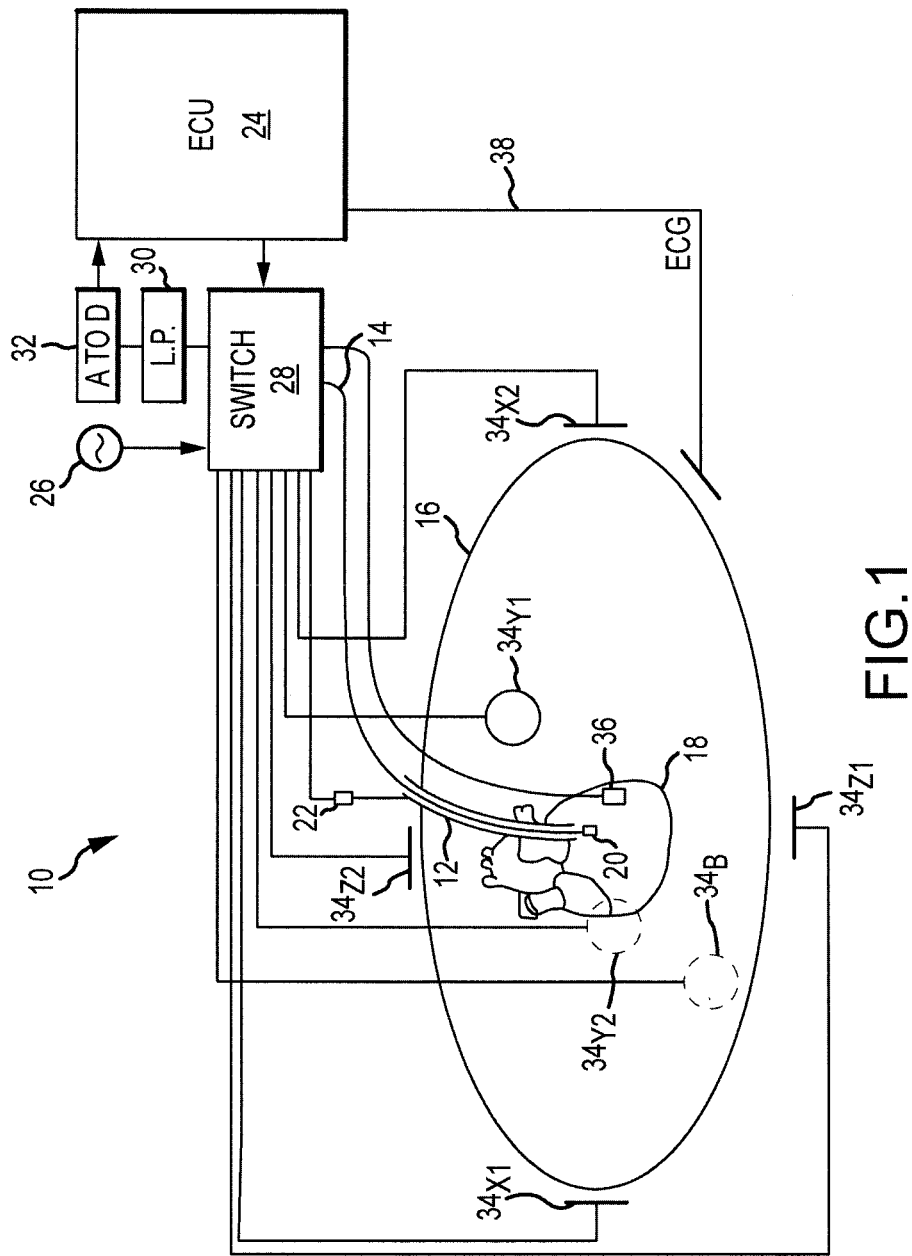
FIG. 1 is a schematic and block diagram view of a system for determining the position and orientation of a medical device and for determining the positions of two coaxial medical devices relative to each other.
Figure 2A:
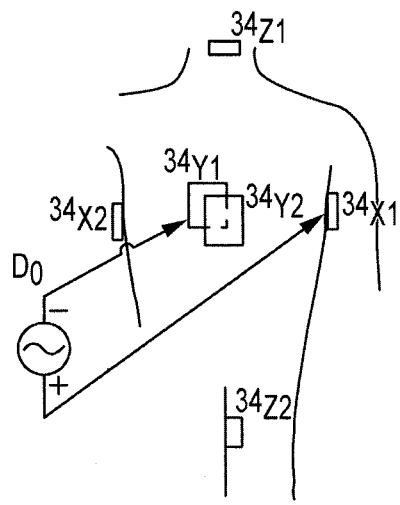
FIGS. 2A-2D are schematic diagrams of exemplary dipole pairs of driven body surface electrodes.
Figure 2B:
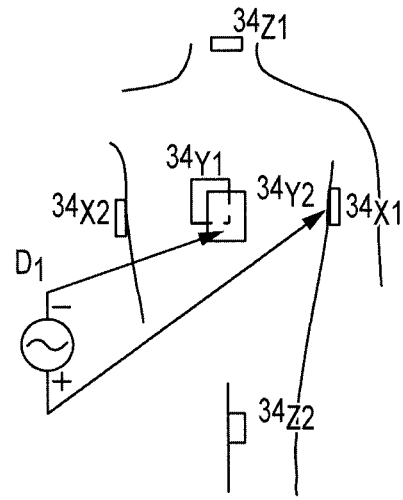
Figure 2C:
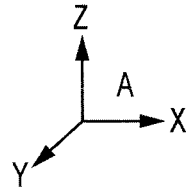
Figure 2C:
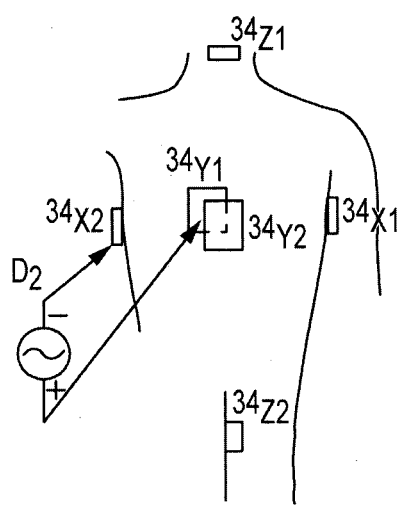
Figure 2D:
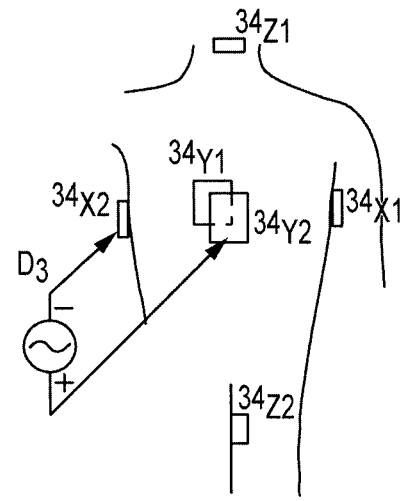

Referring now to the Figures, in which like reference numerals refer to the same or similar features in the various views, FIG. 1 is a schematic and diagrammatic view of an embodiment of a medical device mapping and navigation system 10. The system 10 is shown coupled with a pair of coaxial medical devices 12, 14 that may be guided to and disposed in a portion of a body 16, such as a heart 18. In an embodiment, an exterior one of the coaxial medical devices may be an introducer 12, and an interior one a catheter 14. For ease of description, the coaxial medical devices 12, 14 will be described with reference to an embodiment in which the exterior medical device is an introducer 12 and the interior medical device is a catheter 14, but the coaxial medical devices 12, 14 are not so limited.

With continued reference to FIG. 1, the catheter 14 may include one or more sensors 20 for, e.g., collecting electrophysiology data and/or determining a location of the catheter within the body. The introducer 12 may include a proximal electrode 22 for creating an electrical field within the introducer 12, as further described below. The system 10 may further include, in an embodiment, an electronic control unit (ECU) 24, a signal generator 26, a switch 28, a low-pass filter 30, an analog-to-digital (A-to-D) converter 32, a plurality of body surface electrode patches 34, a distal electrode 36, and a plurality of ECG patches 38.

The system 10 may be provided for visualization, mapping, and/or navigation of distal body structures and may be referred to herein as "the navigation system." The navigation system 10 may comprise an electric field-based system, such as, for example, an EnSite™ Velocity™ cardiac electroanatomic mapping system running a version of EnSite™ NavX™ navigation and visualization technology software commercially available from St. Jude Medical, Inc., of St. Paul, Minn. and as also seen generally by reference to U.S. Pat. No. 7,263,397, or U.S. Patent Application Publication No. 2007/0060833 A1, both hereby incorporated by reference in their entireties as though fully set forth herein. In other exemplary embodiments, the navigation system 10 may comprise systems other than electric field-based systems. For example, the navigation system 10 may comprise a magnetic field-based system such as the Carto™ system commercially available from Biosense Webster, and as generally shown with reference to one or more of U.S. Pat. Nos. 6,498,944; 6,788,967; and 6,690,963, the disclosures of which are hereby incorporated by reference in their entireties as though fully set forth herein. In another exemplary embodiment, the navigation system 10 may comprise a magnetic field-based system based on the MediGuide™ technology available from St. Jude Medical, Inc., and as generally shown with reference to one or more of U.S. Pat. Nos. 6,233,476; 7,197,354; and 7,386,339, the disclosures of which are hereby incorporated by reference in their entireties as though fully set forth herein. In yet another embodiment, the navigation system 10 may comprise a combination electric field-based and magnetic field-based system, such as, for example and without limitation, the system described in pending U.S. patent application Ser. No. 13/231,284, or the Carto™ 3 system commercially available from Biosense Webster, and as generally shown with reference to U.S. Pat. No. 7,536,218, the disclosures of which are hereby incorporated by reference in their entireties as though set fully forth herein. In yet still other exemplary embodiments, the navigation system 10 may comprise or be used in conjunction with other commonly available systems, such as, for example and without limitation, fluoroscopic, computed tomography (CT), and magnetic resonance imaging (MRI)-based systems. For purposes of clarity and illustration only, the navigation system 10 will be described hereinafter as comprising an electric field-based system, such as, for example, the EnSite™ NavX™ system identified above.

The catheter 14 and sensors 20 may be provided for a variety of diagnostic and therapeutic purposes including, for example, electrophysiological studies, pacing, cardiac mapping, and ablation. In an embodiment, the catheter 14 can be an ablation catheter, mapping catheter, or other elongate medical device. The number, shape, orientation, and purpose of the sensors 20 may vary in accordance with the purpose of the catheter 14. In an embodiment, at least one sensor 20 can be an electrode 20. For purposes of illustration, the description below will be with respect to an embodiment in which the sensors comprise one or more electrodes 20, but the disclosure is not limited to such an embodiment.

With the exception of the patch electrode called a "belly patch" $34_B$, the patch electrodes 34 are provided to generate electrical signals used, for example, in determining the position and orientation of the catheter 14 and in the guidance thereof. In one embodiment, the patch electrodes 34 are placed generally orthogonally on the surface of the body 16 and are used to create axes-specific electric fields within the body. For instance, in one exemplary embodiment, patch electrodes $34_{X1}$, $34_{X2}$ may be placed along a first (x) axis. Patch electrodes $34_{Y1}$, $34_{Y2}$ may be placed along a second (y) axis, and patch electrodes $34_{Z1}$, $34_{Z2}$ may be placed along a third (z) axis. Each of the patch electrodes 34 may be coupled to the multiplex switch 28. In an exemplary embodiment, the ECU 24 may be configured, through appropriate software, to provide control signals to the multiplex switch 28 to thereby sequentially couple pairs of electrodes 34 to the signal generator 26. AC (alternating current) excitation of each pair of electrodes 34 (e.g., in either orthogonal or non-orthogonal pairs) generates an electrical field within the patient's body 16 and within an area of interest such as the heart 18. Voltage levels at non-excited electrodes 34, which are referenced to the belly patch $34_B$, may be filtered by the low-pass filter 30 and converted by the A-to-D converter 32 and provided to the ECU 24 for use as reference values. Those values may be used by the ECU 24 to determine a position and orientation of the catheter 14, as further described below. Position and other information may be synchronized with a state of a cardiac cycle according to data received from the ECG patches 38.

As noted above, one or more electrodes 20 are mounted in or on the catheter 14. In an exemplary embodiment, at least one of the electrodes 20 comprises a positioning electrode and is configured to be electrically coupled to the ECU 24. The electrodes 20 may also be referred to herein as internal electrodes and/or positioning electrodes to distinguish the electrodes from the proximal and distal electrodes 22, 36. With an internal positioning electrode 20 electrically coupled to the ECU 24, the electrode 20 may be placed within electrical fields created in the body 16 (e.g., within the heart 18) by exciting the patch electrodes 34. These electrical fields may be distinct from an electrical field created within the introducer for determining the position of an internal positioning electrode relative to the shaft of the introducer, as will be described below. The positioning electrode 20 experiences voltages that are dependent on the position of the positioning electrode 20 relative to the locations of the patch electrodes 34. Voltage measurement comparisons made between the electrode 20 and the patch electrodes 34 (e.g., a voltage taken at the electrode 20 with respect to the belly patch $34_B$) can be used to determine the position of the positioning electrode 20 relative to the heart 18 or other tissue. Movement of the positioning electrode 20 proximate a tissue (e.g., within a chamber of the heart 18) may produce information regarding the geometry of the tissue. This information may be used, for example, to generate models and maps of anatomical structures. Information received from the positioning electrode 20 can also be used to display on a display device the location and orientation of the positioning electrode 20 and/or a portion of the catheter 14 relative to the heart 18 or other tissue. Accordingly, among other things, the ECU 24 of the navigation system 10 may provide a means for generating display signals used to control a display and the creation of a graphical user interface (GUI) on the display.

Because the catheter 14 and the internal electrodes 20 disposed in or on the catheter 14 may be inserted through the introducer 12, one or more of the electrodes 20 may be within the shaft of the introducer 12 within the body 16, including when the system 10 may use the electrodes 20 to collect positioning, EP, and other data. The introducer shaft may be relatively electrically insulative and may present a relatively high impedance compared to body tissue, so readings or measurements made with internal electrodes 20 disposed within the shaft of the introducer 12 (as opposed to extended from a distal opening of the introducer 12) may be inaccurate. Accordingly, it may be desirable to determine whether one or more internal electrodes 20 are disposed within the shaft of the introducer 12 or are outside of (i.e., extended from) the shaft of the introducer 12.

The system 10 may be configured to determine the position of one or more electrodes relative to the introducer. For example, in an embodiment, the system 10 (e.g., the ECU 24) may be configured to determine whether an electrode 20 is within a shaft of the introducer 12 or is extended from a distal end of the shaft of the introducer 12. Accordingly, the proximal electrode 22 and the distal electrode 36 may both be coupled to the switch 28 for an electrical signal to be driven between the proximal electrode 22 (acting as an electrical node, such as one of source or a sink) and the distal electrode 36 (also acting as an electrical node, such as the other of a source and a sink) to create an electrical field within the shaft of the introducer 12. The ECU 24 may be further configured to measure a voltage or electrical potential within that field with one or more electrodes 20 and determine whether one or more electrodes 20 are within or outside of the shaft of the introducer 12 according to a measured voltage or potential. It should be noted that, below, numerous references are made to measurement of a potential and/or a voltage. Unless noted otherwise, such references are to potentials and voltages according to the electric field created by a signal driven between the proximal electrode 22 and the distal electrode 36.

The proximal electrode 22 may be coupled, in an embodiment, to the proximal end of the introducer 12. For example, the proximal electrode 22 may be coupled with an external fluid lumen of the introducer 12 (see FIG. 3), with the handle of the introducer 12 (see FIG. 4), or with a proximal end of the shaft of the introducer 12 (see FIG. 5). Thus, the proximal electrode 22 may be disposed outside the body 16, in embodiments. In other embodiments, the proximal electrode 22 may be disposed within the body 16, such as in a more distal portion of the shaft of the introducer 12 or at a proximal location on catheter 14. The proximal electrode may be disposed, in embodiments, proximal of (i.e., along a path following the shaft of the introducer 12) the distal electrode 36.

The distal electrode 36 may be disposed, in various embodiments, at a distal location on catheter 14, within or near a distal end of the shaft of the introducer 12, otherwise within the body 16, or on the exterior of the body 16. Accordingly, the distal electrode 36 may be coupled with the introducer 12, with another medical device, or otherwise disposed in or on the body 16. In an embodiment, the distal electrode 36 may be disposed on the body as a patch electrode, and/or one or more of the body patch electrodes 34 may be used as the distal electrode 36. As noted above, a current may be driven between the proximal electrode 22 and the distal electrode 36 to create an electrical field within the interior of the shaft of the introducer 12 to determine whether one or more internal electrodes 20 on the catheter 14 are disposed within the introducer 12, as further described in conjunction with FIGS. 5-7.

The ECU 24 may comprise a programmable microprocessor or microcontroller, or may comprise an application specific integrated circuit (ASIC), in an embodiment. The ECU 24 may include a an input/output (I/O) interface through which the ECU 24 may receive a plurality of input signals including, for example, signals generated by patch electrodes 34 and the positioning electrode 20 (among others), and generate a plurality of output signals including, for example, those used to control the switch 28, a display, and/or other user interface components. The ECU 24 may be configured to perform various functions, such as those described in greater detail above and below, with appropriate programming instructions or code (i.e., software). Accordingly, the ECU 24 can be programmed with one or more computer programs encoded on a computer-readable storage medium for performing the functionality described herein. For example, as will be described in conjunction with FIGS. 5-7, the ECU 24 may be configured to assess electrical measurements with one or more of the internal electrodes 20 to determine whether one or more internal electrodes 20 are disposed within or outside of the shaft of the introducer 12.

In operation, as the patch electrodes 34, proximal electrode 22, and distal electrode 36 are selectively energized, the ECU 24 receives position signals (location information) from the catheter 14 (and particularly the internal positioning electrode 20) reflecting changes in voltage levels on the internal positioning electrode 20 and from the non-energized patch electrodes 34. Alternatively, the roles of distal electrode 36 and energized patch electrode 34 may be interchanged for the purpose of determining if one or more internal electrodes 20 are disposed within the introducer 12. The ECU 24 uses the raw positioning data produced by the patch electrodes 34 and internal positioning electrode 20 and may correct the data to account for respiration, cardiac activity, and other artifacts using known techniques. The corrected data may then be used by the ECU 24 in a number of ways, such as, for example and without limitation, to determine whether one or more electrodes 20 are within or outside of the shaft of the introducer 12, to guide the catheter 14 to a diagnosis or treatment site, to create a model of an anatomical structure, to map electrophysiological data on an image or model of the heart 18 or other tissue generated or acquired by the ECU 24, or to create a representation of the catheter 14 that may be superimposed on a map, model, or image of the heart 18 generated or acquired by the ECU 24.

FIGS. 2A-2D show a plurality of exemplary non-orthogonal dipoles, designated $D_0$, $D_1$, $D_2$ and $D_3$, set in a first coordinate system A (i.e., the native coordinate system of the navigation system 10). For any desired axis, the potentials measured across an intra-cardiac positioning electrode 20 resulting from a predetermined set of drive (source-sink) configurations may be combined algebraically to yield the same effective potential as would be obtained by simply driving a uniform current along the orthogonal axes. Any two of the surface electrodes 34 may be selected as a dipole source and drain with respect to a ground reference, e.g., belly patch $34_B$, while the unexcited body surface electrodes measure voltage with respect to the ground reference. The positioning electrode 20 placed in heart 18 is also exposed to the field from a current pulse and is measured with respect to ground, e.g., belly patch $34_B$. In practice, a catheter or multiple catheters within the heart may contain multiple positioning electrodes 20 and each positioning electrode 20 potential may be measured separately.

Data sets from each of the patch electrode 34 and the positioning electrode 20 may be used to determine the location of the positioning electrode 20 within heart 18. After the voltage measurements are made, a different pair of surface electrodes 34 may be excited by the signal generator 26 and the voltage measurement process of the remaining patch electrodes 34 and positioning electrode 20 takes place. The sequence occurs rapidly, e.g., on the order of 100 times per second in an embodiment. To a first approximation the voltage on the positioning electrode 20 within the heart bears a linear relationship with position between the patch electrodes 34 that establish the field within the heart, as more fully described in U.S. Pat. No. 7,263,397 referred to above.

In summary, FIG. 1 shows an exemplary navigation system 10 that employs seven body surface electrodes (patches) 34, which may be used for injecting current and sensing resultant voltages. Current may be driven between two patches 34 at any time; some of those driven currents are illustrated in FIGS. 2A-2D. Measurements may be performed between a non-driven patch and, for example, belly patch $34_B$ as a ground reference. A patch bio-impedance, also referred to as a "patch impedance" may be computed according to the following equation:

$$BioZ[c \rightarrow d][e] = \frac{V_e}{I_{c \rightarrow d}} \quad (1)$$

where $V_e$ is the voltage measured on patch e and $I_{c \rightarrow d}$ is a known constant current driven between patches c and d, where patches c, d, and e may be any of the patch electrodes 34. The position of an internal electrode 20 may be determined by driving current between different sets of patches 34 and measuring one or more patch impedances along with the voltage on the positioning electrode 20. In one embodiment, time division multiplexing may be used to drive and measure all quantities of interest. Position determining procedures are described in more detail in U.S. Pat. No. 7,263,397 and Publication 2007/0060833 referred to above, as well as other references. This position determination procedure may be performed simultaneously with measurements and calculations for determining the position of an internal electrode 20 relative to the shaft of the introducer 12.

Figure 3:
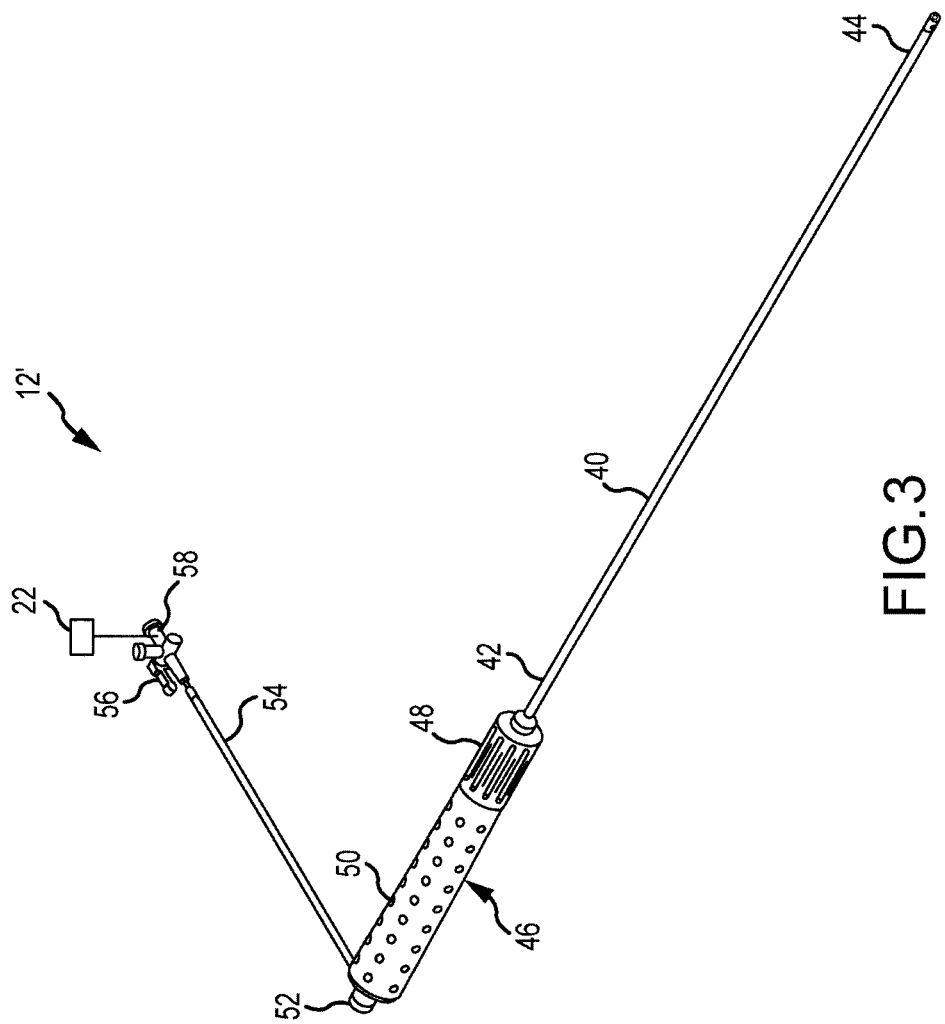
FIG. 3 is a diagrammatic isometric view of an embodiment of an introducer.

FIG. 3 is a diagrammatic isometric view of an embodiment of the introducer 12'. In an exemplary embodiment, the introducer 12' may include a shaft 40 having a proximal end portion 42 and a distal end portion 44, a handle assembly 46 including an adjustment knob 48 and a grip portion 50, a hemostasis valve 52 for insertion of an internal coaxial medical device such as a catheter, an exterior fluid lumen 54 terminating in a stopcock 56, which may also include a Luer taper 58 for connection to an irrigation system (not shown), and the proximal electrode 22. The introducer 12' may further include other conventional components such as, for example and without limitation, one or more position sensors, a temperature sensor, additional sensors or electrodes, ablation elements (e.g., ablation tip electrodes for delivering RF ablative energy, high intensity focused ultrasound ablation elements, etc.), and corresponding conductors or leads. Additionally, the shaft 40 may include one or more fluid lumens extending from the distal end portion 44 to the proximal end portion 42 (and, in an embodiment, into and though the handle assembly for fluid coupling with the exterior fluid lumen 54) for the delivery and/or removal of one or more fluids such as, for example only, irrigation fluids, bodily fluids, and cryogenic ablation fluids. But for the proximal electrode 22, the introducer 12' may be substantially similar to or the same as one or more introducer embodiments illustrated and/or described in U.S. patent application Ser. No. 13/765,128, filed Feb. 12, 2013, which is hereby incorporated by reference in its entirety as though fully set forth herein.

In an embodiment, the proximal electrode 22 may be coupled with the exterior fluid lumen 54 (i.e., with the interior thereof). Accordingly, the proximal electrode 22 may be inserted through a wall of the exterior fluid lumen 54 or may be disposed within the exterior fluid lumen 54 and coupled with leads extending out of the exterior fluid lumen 54. The proximal electrode 22 may thus be electrically coupled with the interior of the exterior fluid lumen 54 and with fluid within the lumen 54. A signal may thus be driven between the proximal electrode 22 and another electrode (e.g., the distal electrode 36, see FIG. 1) to create an electrical field conducted by fluid in the external fluid lumen 54 and fluid lumen within the handle assembly 46 and shaft 40 of the introducer 12'.

The shaft 40 may also include one or more pull wires for deflecting a portion of the shaft 40 such as, for example, the distal end portion 44. Each pull wire may extend through the shaft 40 and be coupled with a pull ring within the shaft 40 or may otherwise be directly or indirectly attached to a portion of the shaft 40 where deflection is desired. Each pull wire may extend through the shaft 40 to the handle assembly 46.

The handle assembly 46 is provided to enable a clinician to guide the distal end portion 44 of the shaft 40 to a target site, such as a location within the heart, to allow another medical device, such as a catheter (see FIGS. 1 and 6) to be passed through the introducer 12' to perform a particular diagnostic and/or therapeutic function. Accordingly, the handle assembly 46 may be coupled with the proximal end portion 42 of the shaft 40 and may comprise an adjustment knob 48 and a grip portion 50. The grip portion 50 may be configured in size, shape, and materials to be comfortably and securely gripped by a clinician guiding the introducer 12'. The adjustment knob 48 may be provided as an exterior mechanism through which a clinician can deflect the shaft 40 such as, for example, the distal end portion 44 of the shaft 40. The adjustment knob 48 may thus be coupled, directly or indirectly, with one or more pull wires (not shown) that extend through the shaft 40.

In an embodiment, the handle assembly 46 may be omitted from the introducer 12'. In such an embodiment, the shaft 40 may terminate (i.e., on its proximal end) in a stopcock 56, which may also include a luer taper 58 for connection to an irrigation system (not shown), and the proximal electrode 22. Accordingly, in different embodiments, the proximal electrode may be coupled directly to the proximal end portion of the shaft 40 or indirectly to the proximal end portion of the shaft 40, such as through a handle assembly 46, a luer taper 58, or another structure.

Figure 4:
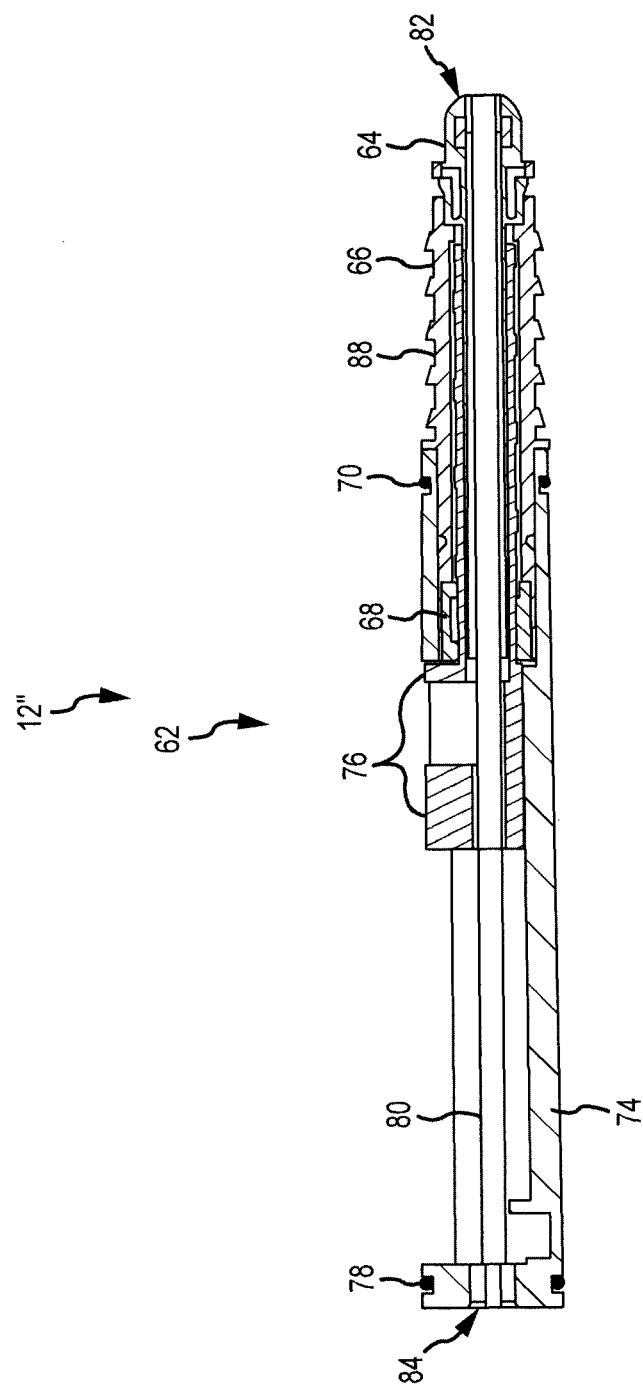
FIG. 4 is a cross-sectional view of an embodiment of an introducer handle.

FIG. 4 is a cross-sectional view of an interior assembly 62 of an alternate embodiment of the introducer 12". The interior assembly 62 may comprise a wire guide 64, an adjustment knob insert 66, a bushing 68, a first O-ring 70, a mounting shaft 74, two slider blocks 76, and a second O-ring 78. An internal fluid lumen 80 may extend through the wire guide 64, the adjustment knob insert 66, and the mounting shaft 74, for coupling with a shaft at the distal end 82 of the interior assembly 62 and an external fluid lumen at the proximal end 84 of the interior assembly (see FIG. 3).

The wire guide 64 may be disposed at the distal end 82 of the interior assembly 64 and extend proximally through the insert 66, the bushing 68, and a portion of the mounting shaft 74. The wire guide 64 may be configured to receive a shaft (i.e., the shaft 40 shown in FIG. 3) and may provide a passage for one or more pull wires and the internal fluid lumen 80 from the handle assembly to the shaft. The wire guide 64 may also provide a passage for other components between the handle assembly and the shaft such as, for example only, electrical leads or wires, the interior fluid lumen, and/or for the passage of other medical devices, such as a catheter and/or guidewire, therethrough.

The adjustment knob insert 66 and bushing 68 may be configured to transfer force (i.e., circumferential force) from an exterior mechanism (i.e., an embodiment of an adjustment knob 48, see FIG. 3) to the slider blocks 76. The slider blocks 76 may be coupled, directly or indirectly, to respective pull wires (not shown) such that longitudinal translation of a slider block 76 places tension on a respective pull wire to deflect the distal end portion of the introducer shaft. The insert 66 may comprise a knob coupling portion 88 including one or more features for securing the insert 66 to the adjustment knob 48 such as, for example only, barbs or a knurled surface. The bushing 68 may be disposed inside the insert 66, and the bushing 68 and insert 66 may include complementary mechanical features so that the bushing 68 and insert 66 rotate in unison.

The proximal electrode 22 may be incorporated into the wire guide 64, in an embodiment, for extension into and electrical coupling with the interior of the internal fluid lumen 80 and electrical coupling with fluid within the internal fluid lumen 80. The proximal electrode 22 may alternatively be incorporated into another component of the interior assembly 62 for extension into the interior of the internal fluid lumen 80. But for the proximal electrode 22, the interior assembly 62 may be substantially similar to or the same as one or more embodiments illustrated and/or described in U.S. patent application Ser. No. 13/765,128, referenced above.

Figure 5:
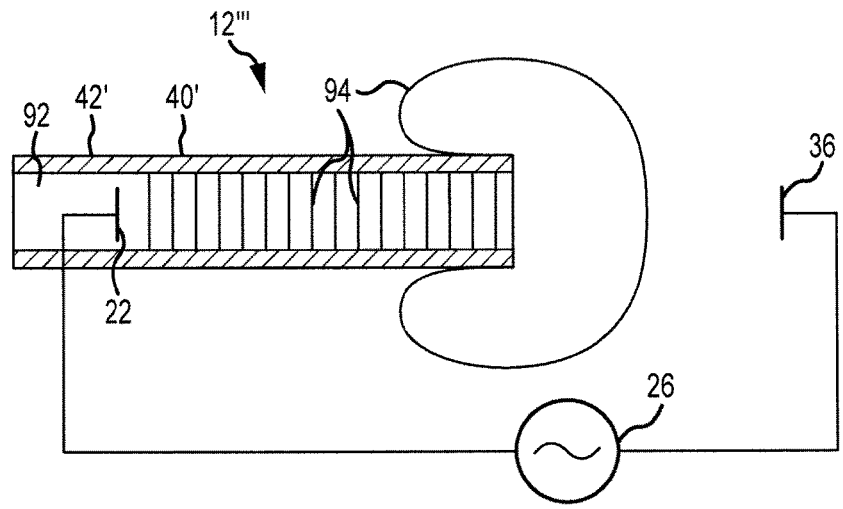
FIG. 5 is a schematic view of an embodiment of system including an introducer for determining the relative positions of one or more electrodes on a second medical device therewithin.

FIG. 5 is a diagrammatic view of a shaft 40' of an alternate embodiment of the introducer 12''' coupled with the signal generator 26, which is also coupled with the distal electrode 36. In the introducer 12''', the proximal electrode 22 may be incorporated into a proximal end portion 42' of the shaft 40'. The proximal electrode 22 may be incorporated into the shaft 40' so that the proximal electrode is electrically coupled with the interior of a fluid lumen 92 within the shaft 40' so that an electrical signal may be driven by the signal generator 26 between the proximal electrode 22 (acting as an electrical node, such as a source or a sink) and a second electrode (i.e., the distal electrode 36) so as to create an electrical field within the interior of the shaft 40' of the introducer 12'''.

In an embodiment, the resistance of the introducer 12''' (including the fluid lumen 92 and any fluid therein) may be significantly higher than the resistance of patient tissue and/or blood pool. For example, the resistance of the introducer 12''' may be significantly higher that the resistance of patient tissue if the introducer 12''' has a length that is much larger than its radius. Accordingly, the electrical potential between the proximal electrode 22 and the distal electrode 36 may drop by a relatively large amount over the length of the introducer shaft 40', and a relatively negligible or nominal amount within the body 16 of the patient, as illustrated by the exemplary isopotential lines 94 in FIG. 5. Thus, a sensing electrode within the shaft 40' of the introducer 12''' may experience and be used to measure an electrical potential that varies significantly according to the location of the sensing electrode along the length of the introducer shaft 40'. This measurement may be used, in an embodiment, to determine the position of the sensing electrode within the introducer 12'''. In contrast, a sensing electrode within the body 16 of the patient, but not within the shaft 40' of the introducer 12''', may measure substantially the same electrical potential regardless of the location of the sensing electrode within the body 16. This contrast may be utilized to determine whether an electrode is within the shaft 40' of the introducer 12''' or extended from the shaft 40'.

Figure 6:
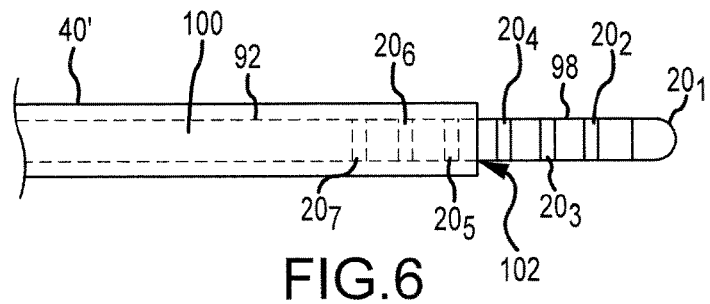
FIG. 6 is a diagrammatic view of a catheter shaft extending from an introducer shaft.

FIG. 6 is a diagrammatic view of a distal end portion 98 of a catheter shaft 100 extending through and out of a distal end opening 102 of the introducer shaft 40'. The catheter shaft 100 may include a number of interior electrodes 20, including a tip electrode $20_1$ and a number of ring electrodes $20_2$, $20_3$, $20_4$, $20_5$, $20_6$, $20_7$. The catheter shaft 100 may extend through a fluid lumen 92 of the shaft 40' of the introducer 12'''. Electrical measurements made with one or more of the electrodes 20 may be used to determine whether one or more of the interior electrodes 20 are within the introducer shaft 40' or outside of the introducer shaft 40', as further described below.

Figure 7:
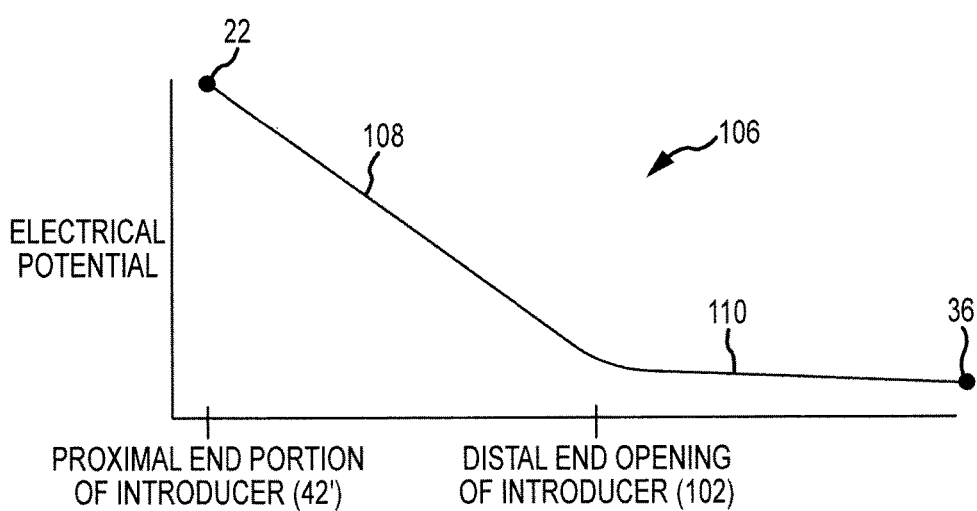
FIG. 7 is a plot illustrating the electric potential that may be detected by an electrode on the catheter shaft of FIG. 6 within and extended from the introducer shaft of FIG. 6.

FIG. 7 is a plot 106 illustrating an exemplary relationship between the position of a sensing electrode (e.g., an interior electrode 20) and the electrical potential measured by that electrode. In an embodiment in which the proximal electrode 22 is the positive polarity terminal for a signal and the distal electrode 36 is a negative polarity terminal for the signal, the electrical potential of the field generated by the signal may decrease from the proximal end portion 42' of the introducer to the distal end opening 102 of the introducer, as shown by the sloped portion 108 of the plot 106. The decrease may be substantially linear, in an embodiment. Of course, in an embodiment, the proximal electrode 22 may alternatively be designated the negative polarity terminal, and the distal electrode 36 the positive polarity terminal, and the electrical potential of the alternating current field generated by the signal may increase from the proximal end portion 42' of the introducer to the distal end opening 102 of the introducer. Furthermore, in an embodiment, the electrical potential change over the length of the introducer shaft 40' may be substantially non-linear and/or may include one or more non-linear portions.

Regardless of the respective polarities of the proximal and distal electrodes 22, 36, substantially the same electrical potential may be present throughout the patient's body (as created by the signal between the proximal electrode 22 and the distal electrode 36), as illustrated by the flat portion 110 of the plot 106. Thus, once an electrode emerges from the introducer shaft 40', it may measure substantially the same electrical potential irrespective of how far it is extended from the introducer shaft 40'.

Referring to FIGS. 5, 6, and 7, an electrical signal may be driven between the proximal electrode 22 and the distal electrode 36 to create an electrical field within the shaft 40' of the introducer 12''' and within an area of the patient's body 16 surrounding the distal end opening 102 of the introducer shaft 40'. As the interior electrodes 20 of the catheter shaft 100 pass through the introducer shaft 40', the electrical potential that may be measured by one of the interior electrodes 20 changes. As shown by the sloped portion 108 of the plot 106 of FIG. 7, this change may be relatively linear along the length of the introducer shaft 40'. As the distal end portion 98 of the catheter shaft 100 extends out of the introducer shaft 40', an interior electrode 20 that is no longer within the introducer shaft 40' may measure approximately the same electrical potential regardless of the distance of the interior electrode 20 from the distal opening 102 of the introducer shaft 40', as shown by the flat portion 110 of the plot 106 of FIG. 7.

In the exemplary configuration illustrated in FIG. 6—i.e., with four interior electrodes $20_1$, $20_2$, $20_3$, $20_4$ outside of the introducer shaft 40' and three interior electrodes $20_5$, $20_6$, $20_7$ inside of the introducer shaft 40'—electric potentials may be measured with one or more of the interior electrodes 20 to determine whether one or more of the interior electrodes 20 are within or outside of the introducer shaft 40'. The four interior electrodes $20_1$, $20_2$, $20_3$, $20_4$ outside of the introducer shaft 40' may each measure substantially the same potential, and the three interior electrodes $20_5$, $20_6$, $20_7$ within the introducer shaft 40' may measure potentials that are different from each other and different from those of the four interior electrodes $20_1$, $20_2$, $20_3$, $20_4$ outside of the introducer shaft 40'.

In an embodiment, each interior electrode 20 may be used to measure an electrical potential according to the electrical field created by the signal driven between the proximal electrode 22 and the distal electrode 36. A single potential—i.e., a unipolar measurement—measured by an interior electrode 20 may be compared to a threshold to determine if the interior electrode 20 is within the introducer shaft 40' or outside of the introducer shaft 40'. In an embodiment, an electrical potential below the threshold may indicate that the interior electrode 20 is outside of the introducer shaft 40'. The threshold may be selected to be slightly higher than the relatively constant electrical potential outside of the introducer shaft 40', in an embodiment in which the potential decreases from the proximal end portion 42' of the introducer to the distal end opening 102. In another embodiment, in which the potential increases from the proximal end portion 42' of the introducer shaft 40' to the distal end opening 102 of the introducer shaft 40', the threshold may be selected to be slightly lower than the relatively constant electrical potential outside of the introducer shaft 40', and a potential value above the threshold may indicate that an internal electrode 20 is outside of the introducer shaft 40'. One or more thresholds may be determined experimentally, mathematically, or otherwise as known in the art.

More than one potential may also be measured—i.e., a multi-polar measurement—to determine whether one or more internal electrodes 20 are within or outside of the introducer shaft 40'. The multi-polar measurement may include a voltage measured between two of the internal electrodes 20 (i.e., a bipolar or differential measurement), such as two adjacent internal electrodes $20_1$, $20_2$, for example only. The voltage may be compared to a threshold to determine whether one or both electrodes 20 are within the introducer shaft 40' or outside of the introducer shaft 40'. In an embodiment, the bipolar voltage may be substantially zero if both electrodes 20 are outside the introducer shaft 40'. The bipolar voltage may be substantially equal to a known or measurable value if both electrodes 20 are inside the introducer shaft 40' (i.e., in an embodiment in which the potential changes linearly over the length of the introducer shaft 40'). The bipolar voltage may be between zero and the known or measurable value if one electrode 20 is inside the introducer shaft 40' and the other outside the introducer shaft 40'. In an embodiment, the threshold for a multi-polar measurement may be slightly more than zero. One or more thresholds may be determined experimentally, mathematically, or otherwise as known in the art.

The methods, systems, and devices described above may be used, in an embodiment, with a remote catheter guidance system (RCGS), such as that described in U.S. Pat. No. 8,343,096, hereby incorporated by reference in its entirety. In such an embodiment, one or both of the interior coaxial medical device and the exterior coaxial medical device may be robotically or otherwise remotely controlled.

Although a number of embodiments of this invention have been described above with a certain degree of particularity, those skilled in the art could make numerous alterations to the disclosed embodiments without departing from the spirit or scope of this invention. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A system comprising: an electronic control unit (ECU), wherein the ECU comprises a processor; and an exterior coaxial elongate medical device coupled with the ECU and configured to be coupled with an interior coaxial medical device having an interior electrode, the exterior coaxial elongate medical device comprising: a shaft having a proximal end portion, a distal end portion, and an interior lumen, said interior lumen configured to receive the interior coaxial medical device therethrough; a proximal electrode coupled with said proximal end portion, said proximal electrode configured to act as a first electrical source or sink; and a distal electrode coupled with said distal end portion, said distal electrode configured to act as a second electrical sink or source, respectively, so as to enable, together with the first electrical source or sink, creation of an electrical field within said interior lumen between said first electrical source or sink and said second electrical sink or source; wherein a position of the interior electrode may be determined, by the ECU, according to said electrical field.

2. A system of claim 1, wherein said proximal end portion is coupled with an exterior fluid lumen, wherein said proximal electrode is coupled with said exterior fluid lumen.

3. A system of claim 1, wherein said interior lumen comprises a fluid lumen, and wherein said proximal electrode and said distal electrode are configured to create the electrical field within said fluid lumen.

4. A system of claim 1, wherein said proximal electrode is disposed within said proximal end portion of said shaft.

5. A system of claim 1, wherein said shaft comprises a body having an impedance that is significantly higher than the impedance of a body of a patient.

6. A method of determining the relative positions of an interior electrode coupled with an interior coaxial medical device and a shaft of an exterior coaxial medical device, the method comprising: driving an electrical current between a proximal electrode coupled with a proximal end of the interior coaxial medical device and a distal electrode so as to create an electrical field within an interior lumen of the exterior coaxial medical device, at least a portion of the interior coaxial medical device disposed within the interior lumen; measuring, by an electronic control unit (ECU), an electrical potential with the interior electrode according to the electrical field, wherein the ECU comprises a processor; and determining, by the ECU, whether the interior electrode is within the shaft of the exterior coaxial medical device according to the measured electrical potential.

7. The method of claim 6, wherein said determining comprises comparing the measured electrical potential to an electrical potential threshold.

8. The method of claim 7, wherein a measured electrical potential above the electrical potential threshold indicates that the interior electrode is within the shaft of the exterior coaxial medical device and a measured electrical potential below the electrical potential threshold indicates that the interior electrode is not within the shaft of the exterior coaxial medical device.

9. The method of claim 6, wherein the interior electrode is a first interior electrode and the interior coaxial medical device further includes a second interior electrode, wherein said measuring comprises measuring a voltage across the first interior electrode and the second interior electrode.

10. The method of claim 9, wherein said determining, by the ECU, comprises comparing the measured voltage to a measured voltage threshold.

11. The method of claim 10, wherein a magnitude of the measured voltage above the measured voltage threshold indicates that at least one of the first interior electrode and the second interior electrode is within the shaft of the exterior coaxial medical device and a magnitude of the measured voltage below the measured voltage threshold indicates that at least one of the first interior electrode and the second interior electrode is not within the shaft of the exterior coaxial medical device.

12. The method of claim 6, wherein the distal electrode is disposed within an interior of a body of a patient.

13. The method of claim 6, wherein the distal electrode is disposed on the exterior of a body of a patient.

14. The method of claim 6, wherein the distal electrode is coupled with the interior coaxial medical device.

15. An electronic control unit (ECU) for determining the position of an interior electrode coupled with an interior coaxial medical device relative to a distal end opening of a shaft of an exterior coaxial medical device, the exterior coaxial medical device including an interior lumen configured to receive the interior coaxial medical device and a proximal electrode, the ECU configured to: drive an electrical current between the proximal electrode and a distal electrode so as to enable creation of an electrical field within the interior lumen of the exterior elongate medical device between the proximal electrode and the distal electrode, wherein the proximal electrode is configured to act as a first electrical source or sink and the distal electrode is configured to act as a second electrical sink or source, respectively; measure an electrical potential with the interior electrode; and determine a position of the interior electrode relative to the distal opening of the exterior elongate medical device shaft according to said measured electrical potential.

16. The ECU of claim 15, wherein the ECU is configured to determine the position by comparing the measured electrical potential to an electrical potential threshold.

17. The ECU of claim 16, wherein the ECU is configured one or more of indicate that the interior electrode is distal of the distal end opening of the exterior coaxial medical device shaft if the measured electrical potential is below the electrical potential threshold and indicate that the interior electrode is proximal of the distal end opening of the exterior coaxial medical device if the measured electrical potential is above the electrical potential threshold.

18. The ECU of claim 15, wherein the interior electrode is a first interior electrode and the ECU is configured to measure a voltage across the first interior electrode and a second interior electrode coupled with the interior coaxial medical device.

19. The ECU of claim 18, wherein the ECU is configured to compare a magnitude of the measured voltage to a voltage threshold and further configured to one or more of indicate that one or more of the first interior electrode and the second interior electrode is distal of the distal end opening of the exterior coaxial medical device if the measured voltage magnitude is greater than the voltage threshold and indicate that one or more of the first interior electrode and the second interior electrode is proximal of the distal end opening of the exterior coaxial medical device if the measured voltage magnitude is less than the voltage threshold.

* * * * *